United States Patent [19]

Patel et al.

[11] 4,361,689

[45] Nov. 30, 1982

[54] CROSS-LINKED HYDROPHILIC POLYMERS

[76] Inventors: Pravin G. Patel, 44, Lockington Crescent, Dunstable, Bedfordshire, England, LU5 45U; Nicholas M. Da Costa, 99, Leafields, Houghton Regis, Bedfordshire, England

[21] Appl. No.: 218,633

[22] Filed: Dec. 18, 1980

Related U.S. Application Data

[63] Continuation-in-part of Ser. No. 89,906, Oct. 31, 1979, abandoned.

[30] Foreign Application Priority Data

Nov. 4, 1980 [GB] United Kingdom ............... 8035366

[51] Int. Cl.³ .............................................. C08F 26/10
[52] U.S. Cl. ..................................... 526/264; 523/108
[58] Field of Search ................ 260/29.6 H, 29.6 HN, 260/29.7 H; 526/264, 312, 320, 323

[56] References Cited

U.S. PATENT DOCUMENTS 4,158,089  6/1979  Loshaek .............................. 526/264
4,182,822  1/1980  Chang ................................. 526/264

*Primary Examiner*—Paul R. Michl
*Attorney, Agent, or Firm*—Lewis H. Eslinger

[57] ABSTRACT

Cross-linked hydrophilic polymers, useful inter alia for the manufacture of contact lenses capable of absorbing water to a water content of 63 to 90% by weight while retaining excellent tensile strength contain hydrophilic units of N-vinyl-2-pyrrolidone, with optionally other hydrophilic monomers in minor amount, hydrophobic units of cycloalkyl acrylate, methacrylate or itaconate, and optionally other hydrophobic monomers, and units of a cross-linking agent. They may be made by polymerizing the monomers in the presence of a free radical generating catalyst. The polymer may then be shaped and hydrated.

6 Claims, No Drawings

CROSS-LINKED HYDROPHILIC POLYMERS

DESCRIPTION

This Application is a Continuation-in-Part of our Application Ser. No. 89906 filed Oct. 31, 1979 now abandoned.

This invention relates to cross-linked hydrophilic polymers and their preparation and use.

A wide variety of hydrophilic polymers have been prepared for use in making so called "soft" contact lenses but none of the materials currently in use has proved entirely satisfactory because of the strict requirements for an ideal polymer. Thus the polymer must have, when hydrated for use, a high permeability to water and oxygen, so that it can be worn for prolonged periods without damage to the cornea, combined with good tensile strength, so that the lens made from the polymer can be easily handled without damage. In addition, of course, the polymer must be substantially colourless and transparent. These requirements are to some extent incompatible and it has in particular provided difficult or impossible heretofore to provide hydrated polymers having both a high permeability to water and oxygen and adequate tensile strength. Equally it has been difficult to combine the preferred elongation at break with adequate tensile strength.

Because of the difficulty in producing entirely satisfactory polymers for soft (hydrophilic) contact lenses, there have been numerous proposals in the patent literature of polymers said to have properties which are advantageous in one or more ways. Examples of such patents are U.S. Pat. Nos. 3,503,942, 3,532,679, 3,878,175, 3,965,063, 4,022,754, 4,032,599, 4,036,814, 4,038,264, 4,158,089, 4,182,802 and 4,182,822.

The present invention provides hydrophilic polymers capable of being hydrated to give clear hydrated polymers which, in their preferred form, combine to a satisfactory extent the desired properties of permeability, tensile strength and clarity.

High permeability to water and oxygen are provided by a high water content, but a high water content in general reduces tensile strength. However, to some extent a high water content reduces the requirement for high tensile strength and vice versa. This is because the stronger the polymer, the thinner the soft contact lens can be made. Since permeability is inversely proportional to thickness a thin lens of high tensile strength polymer can have the same permeability to water and oxygen as a thicker lens of lower tensile strength polymer. Nevertheless in practical terms there are both lower and upper practical limits on the thickness of soft contact lenses and hence on the permeability requirements of the polymers from which they are made.

The valuable properties of the copolymers of the present invention are dependent inter alia on the use, as the predominant, if not the only, hydrophilic monomer, of N-vinyl-2-pyrrolidone, and on including in the copolymer a cycloalkyl acrylate or methacrylate. This combination, essential for the success of the present invention, is nowhere proposed in the prior specifications mentioned above, except that U.S. Pat. No. 4,182,822 does disclose cyclohexyl methacrylate as a possible comonomer, along with many others, in copolymers which essentially contain residues of a monomer such as N-vinyl-2-pyrrolidone and a polysiloxanyl acrylate or methacrylate monomer. Of the other U.S. Pat. Nos. 3,503,942 and 3,965,063 do not refer to the use of N-vinyl-2-pyrrolidone, and, while they do refer to the possibility of using cyclohexyl methacrylate as a comonomer, the latter is not differentiated from various other hydrophobic comonomers not having, in the context of the present invention, the same valuable properties as the cycloalkyl monomers. The remaining patents disclose the use of N-vinyl-2-pyrrolidone as a comonomer, and while a wide variety of other possible comonomers, both hydrophilic and hydrophobic, are disclosed, there is no disclosure of any cycloalkyl acrylate or methacrylate as a possible comonomer. While it might be thought that a partially cross-linked copolymer of N-vinyl-2-pyrrolidone and cyclohexyl methacrylate would have much the same properties as a similar copolymer of N-vinyl-2-pyrrolidone and methyl methacrylate (the use of which is often disclosed in the prior patents) in practice we have found that this is not the case, as is illustrated by the results of experiments reported below.

Thus, the essential features of the copolymers of the present invention are not taught in the prior art referred to above.

The present invention accordingly provides a cross-linked hydrophilic polymer capable of absorbing water to give a clear hydrated polymer containing 63 to 90% by weight of water and having a tensile strength of at least 10 g./mm$^2$, the permeability to oxygen and tensile strength of the said hydrated polymer being sufficient for forming contact lenses therefrom, the said polymer comprising hydrophilic units of N-vinyl-2-pyrrolidone and hydrophobic units of a cycloalkyl acrylate, methacrylate or itaconate, the said cycloalkyl containing 5 to 7 ring carbon atoms and being unsubstituted or substituted by alkyl of 1 to 4 carbon atoms, in relative proportions by weight from 88:12 to 97:3, together with 0 to 30% by weight of the N-vinyl-2-pyrrolidone of units of 2-hydroxyethyl or 2-hydroxypropyl acrylate or methacrylate; and 0 to 50% by weight of the N-vinyl-2-pyrrolidone, of units of one or more alkyl or alkoxyalkyl acrylates, methacrylates, maleates, fumarates, or itaconates, the said alkyl or alkoxyalkyl having up to 7 carbon atoms in a straight or branched chain; and units of a copolymerisable cross-linking agent in a proportion of 0.2 to 0.8 parts per 100 parts by weight of the other monomers, the said proportion being sufficient to confer adequate tensile strength and clarity on the hydrated polymer. Preferably in the hydrated polymer the tensile strength is related to the water content, and therefore the permeability to oxygen, so that the tensile strength is at least $(154-1.6x)$ g./mm$^2$ where x is the water content as a percentage by weight.

These new polymers have excellent shape and volume stability when swollen in water or isotonic saline. Preferred polymers in accordance with the present invention have a water content on hydration of 70 to 85% by weight, a tensile strength of at least 35 g./mm$^2$, and an elongation at break of at least 80%. The new polymers are particularly suitable for use in contact lenses but can also be used as dialysis membranes, surgical implants, prosthetic devices and carriers for sustained or slow release of flavours and medicaments.

According to a feature of the invention, the new polymers are made by polymerising together, in the presence of a free radical generating catalyst, the various monomers and the cross-linking agent, the polymerisation being effected first at a relatively low temperature so as to gel the mixture of monomers and then at a higher temperature to complete the copolymerisation. It is important to ensure complete polymerisation of the monomer mixture, e.g. by prolonged heating at elevated temperature. The polymer may then be shaped and finally hydrated in water or isotonic saline to a water content of 63 to 90% by weight.

The cross-linking agent used in preparing the hydrophilic polymer may be any suitable copolymerisable monomer containing two or more copolymerisable ethylenic double bonds. Many such monomers are known in the art. Examples are ethylene glycol dimethacrylate, triethylene glycol dimethacrylate, tetraethylene glycol dimethacrylate, polyethylene glycol dimethacrylate, divinyl benzene, allyl acrylate and allyl methacrylate. It is important to use enough of the cross-linking agent since with some combinations of monomers use of too little cross-linking agent leads to a polymer which is not of adequate clarity.

In some cases, it may be advantageous to use cross-linking agents having three ethylenically unsaturated groups, two of which differ significantly in reactivity from the third. Such cross-linking agents can be used to effect a two-stage or delayed cure, and can produce materials of superior properties when compared with otherwise similar polymers made using cross-linking agents where the reactivity of the double bonds is nearly the same or cross-linking agents with only two ethylenically unsaturated groups of different reactivities. The preferred such cross-linking agents are esters of ethylenically unsaturated polycarboxylic acids having (in the acid residue) up to 6 carbon atoms, in which at least two of the esterifying radicals are allyl radicals. Especially preferred is diallyl itaconate where the reactivity of the acrylic double bond is much higher than that of the allyl groups. Other suitable cross-linking agents of this type are diallyl fumarate, diallyl maleate, allyl vinyl maleate, diallyl aconitate, and divinyl citraconate.

The hydrophilic monomer used in the present invention is at least about 77% N-vinyl-2-pyrrolidone. Other hydrophilic monomers have been found to give inferior results except that up to 30% of the N-vinyl-2-pyrrolidone can be replaced by 2-hydroxyethyl or 2-hydroxypropyl acrylate or methacrylate without serious detriment to the properties of the product.

The cycloalkyl acrylates, methacrylates and itaconates which are used in the present invention may be represented by the formula:

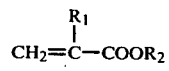

in which $R_1$ is H, $CH_3$ or —$CH_2COOR_2$ and $R_2$ is a cyclic aliphatic group of 5 to 7 ring carbon atoms optionally substituted by alkyl of 1 to 4 carbon atoms. Examples of such monomers are cyclopentyl methacrylate, cyclohexyl methacrylate, and dicyclohexyl itaconate. The presence of this comonomer is essential for the success of the present invention since without it the desired combination of high tensile strength and high water content for the hydrated polymer cannot be achieved.

The optical other hydrophobic comonomers may, in the case of the acrylates, methacrylates and itaconates, be represented by the formula:

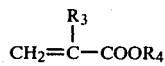

where $R_3$ is H, $CH_3$ or —$CH_2COOR_4$ and $R_4$ is a straight or branched saturated alkyl or alkoxyalkyl radical of up to 7 carbon atoms. Examples of these hydrophobic monomers are methyl methacrylate, ethyl methacrylate, methoxyethyl methacrylate, ethoxyethyl methacrylate, dimethyl itaconate, and diethyl itaconate. Examples of other hydrophobic monomers which are suitable are dimethyl maleate, diethyl maleate, dimethyl fumarate, and diethyl fumarate. These optional hydrophobic monomers can be used either by themselves or as mixtures, and preferably constitute no more than 3 to 18% by weight of the polymer.

The free radical catalyst employed may be, for example, lauryl peroxide, benzoyl peroxide, isopropyl peroctoate, isopropyl peroxydicarbonate, t-butyl perpivalate, or azo-bis-isobutyrodinitrile, the last being preferred.

Preferably the new polymers comprise units of N-vinyl-2-pyrrolidone, cyclohexyl methacrylate, and optionally methyl methacrylate or dimethyl itaconate. The cross-linking agent is preferably allyl methacrylate, ethylene glycol dimethacrylate, tetraethylene glycol dimethacrylate, diallyl itaconate, diallyl maleate, or diallyl fumarate.

The invention is illustrated in the following Examples.

EXAMPLES 1–5

To the mixture of monomers as specified in Table I below was added the specified amount of the cross-linking agent and 0.25% azo-bis-isobutyrodinitrile as free radical generating catalyst. The mixture was placed in a polypropylene mould and sealed. Polymerisation was effected by a two-stage process: the first stage in a constant temperature enclosure at 30°–50° C. for a period sufficient to polymerise the monomers to a tacky semi-solid state (4 to 7 hours) followed by curing at 100°–120° C. in an oil bath (16 to 20 hours) to complete the cross-linking and polymerisation process.

The water content and tensile properties of the copolymers obtained are shown in Table I. The water contents of the polymers were measured in isotonic saline (0.9% NaCl by weight in distilled water at pH 6.6) at 20° C. and expressed as a percentage of water in the hydrated polymer.

$$\text{Water content} = 100 \times \frac{\text{hydrated wt.} - \text{dry wt.}}{\text{hydrated wt.}}$$

TABLE I

| Example No. | Copolymer Wt. Ratio | Monomers | Cross-linking Agent | Water Content at 20° C. | Tensile Strength g./mm² |
|---|---|---|---|---|---|
| 1 | 95/5 | VP/cyclohexyl methacrylate | Diallyl itaconate | 81 | 40 |
| 2 | 82/9/9 | VP/cyclohexyl methacrylate/ methyl methacrylate | Diallyl itaconate | 79 | 50 |
| 3 | 80/13/7 | VP/dimethyl itaconate/dicyclohexyl itaconate | Diallyl itaconate | 76 | 58 |
| 4 | 95/5 | VP/cyclohexyl methacrylate | Diallyl fumarate | 81 | 40 |

TABLE I-continued

| Example No. | Co-polymer Wt. Ratio | Monomers | Cross-linking Agent | Water Content at 20° C. | Tensile Strength g./mm² |
|---|---|---|---|---|---|
| 5 | 95/5 | VP/cyclohexyl methacrylate | Diallyl maleate | 81 | 40 |

VP = N—vinyl-2-pyrrolidone

EXAMPLES 6–31

The mixture of monomers and cross-linking agent, as specified in Table below, is accurately weighed out and thoroughly mixed with the catalyst (azo-bis-isobutyrodinitrile in a proportion of 0.25% by weight of the monomer mixture). The mixture is then placed in polyolefin tubes each 12 to 15 mm. in diameter and sealed at both ends. The sealed tubes are placed in a circulating water bath at a temperature of 25° to 50° C. until the polymer gels. The blocks of polymer are then placed in an oven at 60° C. for 1 hour and the polymer is then removed from the polyolefin tube. The polymer rods then obtained are cured at 110° C. until polymerisation is complete.

Data obtained from various mixtures of monomers in accordance with the present invention are contained in the Tables II to IV below.

TABLE II

| Example No. | Monomers | Weight Ratio | Cross-linking Agent | Parts of cross-linking Agent per 100 parts by weight of other monomers | Water Content % | Tensile Strength g./mm² | Elongation at break % |
|---|---|---|---|---|---|---|---|
| 6 | VP/CHM | 97/3 | AMA | 0.5 | 87 | 20 | 115 |
| 7 | VP/CHM | 96/4 | AMA | 0.5 | 86.5 | 26 | 103 |
| 8 | VP/CHM | 93/7 | AMA | 0.7 | 84 | 38 | 81 |
| 9 | VP/CHM | 91/9 | AMA | 0.9 | 81.5 | 50 | 60 |
| 10 | VP/CHM | 88/12 | AMA | 1.2 | 73 | 71 | 60 |

VP N—vinyl-2-pyrrolidone
CHM cyclohexyl methacrylate
AMA allyl methacrylate

TABLE III

| Example No. | Monomers | Weight Ratio | Cross-linking Agent | Parts of Cross-linking Agent per 100 parts by weight of other monomers | Water Content % | Tensile Strength g./mm² | Elongation at Break % |
|---|---|---|---|---|---|---|---|
| 11 | VP/CHM/MMA | 80/5/15 | AMA | 0.3 | 77.5 | 37 | 165 |
| 12 | VP/CHM/MMA | 82/6/14 | AMA | 0.3 | 78.7 | 35 | 136 |
| 13 | VP/CHM/MMA | 83/7/13 | AMA | 0.3 | 77.0 | 59 | 172 |
| 14 | VP/CHM/MMA | 85/7/13 | DAM | 0.33 | 74.4 | 39 | 88 |
| 15 | VP/CHM/MMA | 83/8/12 | AMA | 0.3 | 77.0 | 52 | 147 |
| 16 | VP/CHM/MMA | 85/8/12 | AMA | 0.3 | 79.1 | 44 | 156 |
| 17 | VP/CHM/MMA | 85/8/12 | EDGMA | 0.3 | 79.7 | 65 | 175 |
| 18 | VP/CHM/MMA | 85/8/12 | TEGDMA | 0.5 | 80.5 | 78 | 209 |
| 19 | VP/CHM/MMA | 84/9/11 | AMA | 0.3 | 76.9 | 77 | 164 |
| 20 | VP/CHM/MMA | 85/10/10 | AMA | 0.3 | 77.0 | 64 | 146 |
| 21 | VP/CHM/MMA/DMM | 80/7/11/2 | AMA | 0.3 | 77.8 | 52 | 160 |
| 22 | VP/CHM/MMA/DBM | 80/7/10/3 | AMA | 0.3 | 77.6 | 50 | 174 |
| 23 | VP/CHM/MMA/DBM | 80/7/8/5 | AMA | 0.3 | 78.0 | 42 | 165 |

MMA Methyl methacrylate
DMM Dimethyl maleate
DBM Dibutyl maleate
DAM Diallyl maleate
EGDMA Ethylene glycol dimethacrylate
TEGDMA Tetraethylene glycol dimethacrylate

TABLE IV

| Example No. | Monomers | Weight Ratio | Cross-linking Agent | Parts of cross-linking Agent per 100 parts by weight of the monomers | Water Content % | Tensile Strength g./mm² | Elongation at Break % |
|---|---|---|---|---|---|---|---|
| 24 | VP/MMA/DCHI | 80/15/5 | AMA | 0.3 | 77 | 41 | 125 |
| 25 | VP/MMA/CHM/HEMA | 60/11.25/3.75/25 | AMA | 0.4 | 67 | 50 | 150 |
| 26 | VP/CHM/EMA | 82/6/14 | AMA | 0.4 | 78 | 36 | 138 |
| 27 | VP/CHM/DMI | 80/8/12 | AMA | 0.4 | 76 | 47 | 132 |
| 28 | VP/CHM/MMA/EEMA | 65/5/12/18 | AMA | 0.5 | 68 | 90 | 148 |
| 29 | VP/CHM/MMA/EEMA | 60/10/15/15 | AMA | 0.5 | 62 | 200 | 135 |
| 30 | VP/CHM/MMA/MEMA | 65/5/12/18 | AMA | 0.5 | 64 | 110 | 143 |
| 31 | VP/CHM/MMA/EEMA | 65/5/15/15 | AMA | 0.5 | 67 | 110 | 150 |

TABLE IV-continued

| Example No. | Monomers | Weight Ratio | Cross-linking Agent | Parts of cross-linking Agent per 100 parts by weight of the monomers | Water Content % | Tensile Strength g./mm² | Elongation at Break % |
|---|---|---|---|---|---|---|---|
| 32 | VP/CHM/HEMA | 72/14/14 | DAM | 0.8 | 70 | 115 | 145 |

DCHI Dicyclohexyl itaconate
HEMA Hydroxylethyl methacrylate
EMA Ethyl methacrylate
DMI Dimethyl itaconate
EEMA Ethoxyethyl methacrylate
MEMA Methoxyethyl methacrylate The tensile strengths were measured on an Instron (Registered Trade Mark) test machine.

The hydrophilic polymers described in the above Examples can easily be fabricated into shaped articles such as contact lenses by lathing techniques.

COMPARATIVE EXAMPLES

A variety of polymers have been made with mixtures of monomers similar to those used in the present invention except that no cycloalkyl acrylate or methacrylate was included. Data for some of the polymers which have been made are contained in the following Table. Examples A to D were made as described in U.S. Pat. No. 4,158,089 (see Examples 6, 8, 9, and 12 thereof). Examples E to N were made by the technique described above for Examples 6-31.

The results given in the Table show that while some of the polymers have a fairly high tensile strength and others have a high water content, it was not possible to obtain polymers having, at one and the same time, a high water content combined with high tensile strength.

TABLE V
COMPARATIVE EXAMPLES

| Example No. | Monomers | Weight Ratio | Cross-linking Agent | Parts of Cross-linking Agents per 100 parts by weight of the monomers | Water Content % | Tensile Strength g./mm² | Elongation at Break % |
|---|---|---|---|---|---|---|---|
| A | VP/MMA | 95/5 | DAI | 0.2 | 89.3 | 7.11 | 133 |
| B | VP/MMA | 85/15 | DAI | 0.15 | 86 | 13.17 | 179 |
| C | VP/MMA | 85/15 | DAI | 0.5 | 80.5 | 23.84 | 108 |
| D | VP/MMA | 80/20 | DAI | 1.0 | 72 | 36.18 | 62 |
| E | VP/MMA | 70/30 | AMA | 0.3 | 68 | 36 | |
| F | VP/MMA | 75/25 | AMA | 0.3 | 76 | 27 | |
| G | VP/MMA | 80/20 | AMA | 0.3 | 80 | 16 | |
| H | VP/MMA | 85/15 | AMA | 0.3 | 82 | 10 | |
| I | VP/MMA | 85/15 | DAM | 0.15 | 86 | 13 | |
| J | VP/MMA | 85/15 | DAM | 0.5 | 80 | 22 | |
| K | VP/MMA | 80/20 | DAM | 1.0 | 72 | 35 | |
| L | VP/Acrylonitrile | 82/18 | DAM | 0.4 | 78 | 15 | |
| M | VP/HEMA | 60/40 | EGOMA | 0.4 | 75 | 10 | |
| N | VP/EEMA | 70/30 | AMA | 0.4 | 68 | 30 | |
| O | VP/MMA/HEMA | 72/14/14 | DAM | 0.8 | 73 | 20 | 90 |
| P | VP/MMA/EEMA | 65/20/15 | AMA | 0.5 | 68 | 40 | 120 |

We claim:

1. A cross-linked hydrophilic polymer capable of absorbing water to give a clear hydrated polymer containing about 63 to 90% by weight of water and having a tensile strength of at least 10 g./mm², the tensile strength being at least (154-1.6x) g./mm² where x is the water content as a percentage by weight and the permeability to oxygen and tensile strength of the said hydrated polymer being sufficient for forming contact lenses therefrom, the said polymer comprising hydrophilic units of N-vinyl-2-pyrrolidone and 0. to 30% by weight of the N-vinyl-2-pyrrolidone of 2-hydroxyethyl or 2-hydroxypropyl acrylate or methacrylate and hydrophobic units of a cycloalkyl acrylate, methacrylate or itaconate, the said cycloalkyl containing 5 to 7 ring carbon atoms and being unsubstituted or substituted by alkyl of 1 to 4 carbon atoms, in relative proportions of the said hydrophobic units to the said hydrophilic units by weight from about 86:14 to 97:3; and 0 to 50% by weight of the N-vinyl-2-pyrrolidone, of units of one or more alkyl or alkoxyalkyl acrylates, methacrylates, maleates, fumarates, or itaconates, the said alkyl or alkoxyalkyl having up to 7 carbon atoms in a straight or branched chain; and units of a copolymerisable cross-linking agent in a proportion of 0.2 to 0.8 parts per 100 parts by weight of the other monomers, the said proportion being sufficient to confer adequate tensile strength and clarity on the hydrated polymer.

2. A hydrophilic polymer according to claim 1 consisting essentially of hydrophilic units of N-vinyl-2-pyrrolidone; hydrophobic units of cyclohexyl methacrylate, with or without methyl methacrylate and/or dimethyl itaconate; and cross-linking units of diallyl itaconate, diallyl maleate, and/or diallyl fumarate.

3. A hydrophilic polymer according to claim 1 consisting essentially of hydrophilic units of N-vinyl-2-pyrrolidone in a proportion of 88 to 97% by weight of the polymer; hydrophobic units of cyclohexyl methacrylate in a proportion of 3 to 12% by weight of the polymer, with or without methyl methacrylate or dimethyl itaconate in a proportion of 3 to 18% by weight of the polymer, the said polymer having on hydration a water content of 70 to 85% by weight and a tensile strength of at least 35 g./mm².

4. A hydrophilic polymer according to claim 1, wherein the cross-linking agent is allyl methacrylate, ethylene glycol dimethacrylate, tetraethylene glycol dimethacrylate, diallyl itaconate, diallyl maleate or diallyl fumarate.

5. A soft contact lens made from a hydrated hydrophilic polymer as claimed in any one of claims 1 to 5.

6. A hydrophilic polymer according to any one of claims 1 to 5 hydrated to a water content of 63 to 90% by weight.

* * * * *